United States Patent
Klein et al.

(10) Patent No.: US 8,278,312 B2
(45) Date of Patent: Oct. 2, 2012

(54) IMIDAZO 1,2-A PYRIMIDINE DERIVATIVES FOR THE TREATMENT OF DISEASES SUCH AS DIABETES

(75) Inventors: Markus Klein, Darmstadt (DE); Werner Mederski, Zwingenberg (DE); Christos Tsaklakidis, Weinheim (DE); Norbert Beier, Reinheim (DE)

(73) Assignee: Merck Patent Gesellschaft mit Beschränkter Haftung, Darmstadt (DE)

( * ) Notice: Subject to any disclaimer, the term of this patent is extended or adjusted under 35 U.S.C. 154(b) by 170 days.

(21) Appl. No.: 12/682,316

(22) PCT Filed: Sep. 13, 2008

(86) PCT No.: PCT/EP2008/007583
§ 371 (c)(1),
(2), (4) Date: Apr. 9, 2010

(87) PCT Pub. No.: WO2009/049731
PCT Pub. Date: Apr. 23, 2009

(65) Prior Publication Data
US 2010/0249151 A1    Sep. 30, 2010

(30) Foreign Application Priority Data
Oct. 11, 2007  (DE) .......................... 10 2007 048 716

(51) Int. Cl.
*A01N 43/90*     (2006.01)
*A61K 31/519*    (2006.01)
*C07D 487/00*    (2006.01)

(52) U.S. Cl. ..................................... 514/259.1; 544/281

(58) Field of Classification Search ........................ None
See application file for complete search history.

(56) References Cited

U.S. PATENT DOCUMENTS
2004/0023972 A1    2/2004  Sundermann et al.

FOREIGN PATENT DOCUMENTS
DE    100 50 663 A1    4/2002
EP    1 964 841 A1    9/2008

OTHER PUBLICATIONS

International Search Report of PCT/EP2008/007583 (Feb. 20, 2009).
Database Chemcats Chemical Abstracts Service, XP002515960 & "Chemdiv Discovery Chemistry Collection", Jul. 1, 2008.

*Primary Examiner* — Jeffrey Murray
(74) *Attorney, Agent, or Firm* — Millen, White, Zelano & Branigan, P.C.

(57) ABSTRACT

Novel compounds of the formula (I), in which W, T, $R^1$, $R^2$, $R^3$, $R^4$, $R^5$, $R^6$ and $X_7$ have the meanings indicated in Patent Claim 1, are suitable as antidiabetics.

4 Claims, No Drawings

IMIDAZO 1,2-A PYRIMIDINE DERIVATIVES FOR THE TREATMENT OF DISEASES SUCH AS DIABETES

The invention relates to compounds of the formula I

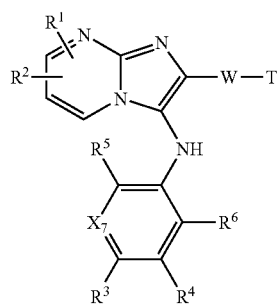

in which
W denotes

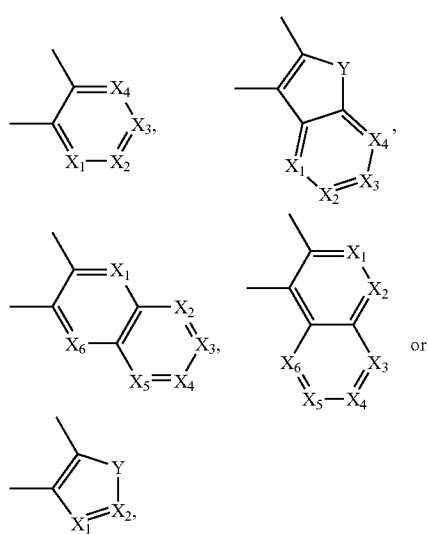

$X_1$, $X_2$, $X_3$,
$X_4$, $X_5$, $X_6$ each, independently of one another, denote $C-R^7$, N or C-Het,
Y denotes O, S, $N-R^7$ or N-Het,
$R^1$, $R^2$, $R^3$, $R^4$,
$R^5$, $R^6$, $R^7$ each, independently of one another, independently denote H, A, OH, OA, NAA', Hal, CN, $NO_2$, $O(CH_2)_m$CONAA', $NA(CH_2)_m$CONAA', $(CH_2)_m$NAA', $O(CH_2)_m$NAA', $O(CH_2)_m$OA, $O(C=O)(CH_2)_m$NAA', $(C=O)O(CH_2)_m$NAA', $NA(C=O)(CH_2)_m$NAA', $(C=O)NA(CH_2)_m$NAA', $CH_2O(CH_2)_m$NAA', $CH_2OA$ or $COOA$,
A, A', A" each, independently of one another, denote H, linear or branched alkyl having 1-10 C atoms which is unsubstituted or mono-, di- or trisubstituted by =S, =NR, =O (carbonyl oxygen), NRR', OH, CN, CONRR' and/or $NO_2$, in which one, two or three $CH_2$ groups may be replaced, independently of one another, by O, S, SO, $SO_2$, NR, —OCO—, —NRCONR'—, —NRCO—, —COO—, —CONR—, —C≡C— groups and/or by —CH=CH— groups and/or, in addition, 1-20 H atoms may be replaced by F and/or Cl, or cyclic alkyl having 3-7 C atoms which is unsubstituted or mono-, di- or trisubstituted by =S, =NR, =O (carbonyl oxygen), NRR', OH, CN, CONRR' and/or $NO_2$, in which one, two or three $CH_2$ groups may be replaced, independently of one another, by O, S, SO, $SO_2$, NR, —OCO—, —NRCONR'—, —NRCO—, —COO—, —CONR—, —C≡C— groups and/or by —CH=CH— groups and/or, in addition, 1-11H atoms may be replaced by F and/or Cl,
R, R',
R", R''' each, independently of one another, denote H, linear or branched alkyl having 1-10 C atoms which is unsubstituted or mono-, di- or trisubstituted by =S, =NR, =O (carbonyl oxygen), $NH_2$, OH, CN, $CONH_2$ and/or $NO_2$, in which one, two or three $CH_2$ groups may be replaced, independently of one another, by O, S, SO, $SO_2$, NH, $NCH_3$, —OCO—, —NHCONH—, —NHCO—, —COO—, —CONH—, —$NCH_3$CO—, $CONCH_3$—, —C≡C— groups and/or by —CH=CH— groups and/or, in addition, 1-20H atoms may be replaced by F and/or Cl, or cyclic alkyl having 3-7 C atoms which is un-substituted or mono-, di- or trisubstituted by =S, =NR, =O (carbonyl oxygen), $NH_2$, OH, CN, $CONH_2$ and/or $NO_2$, in which one, two or three $CH_2$ groups may be replaced, independently of one another, by O, S, SO, $SO_2$, NH, $NCH_3$, —OCO—, —NHCONH—, —NHCO—, —COO—, —CONH—, —$NCH_3$CO—, $CONCH_3$— and/or by —CH=CH— groups and/or, in addition, 1-11H atoms may be replaced by F and/or Cl,
T denotes Het, COOR, CONRR', CONRNRR', CONROR' (hydroxamic acid), $O(CH_2)_m$CONRR', $(CH_2)_m$CONRR', $NR(CH_2)_m$CONR'R"$, $O(CH_2)_m$OCONRR', $(CH_2)_m$O-CONRR', $NR(CH_2)_m$OCONR'R"$, $O(CH_2)_m$NRCONR'R"$, $(CH_2)_m$NRCONR'R"$ or $NR(CH_2)_m$NR'CONR"R''',
Het denotes a mono- or bicyclic saturated, unsaturated or aromatic heterocycle having 1 to 4 N, O and/or S atoms, which may be mono-, di- or trisubstituted by A, Hal, OA, OH, SA, NAA', SOA, $SO_2A$, $NO_2$, CN, COOA, COOH, CHO, COA, $SO_3H$ OCOA, CONAA', NA'COA, NACONA'A", $NA'SO_2A$, $SO_2NAA'$, =S, $=NR^1$ and/or =O (carbonyl oxygen),
Hal denotes F, Cl, Br or I,
m denotes 1, 2 or 3,
and pharmaceutically usable salts and stereoisomers thereof, including mixtures thereof in all ratios.

The invention was based on the object of finding novel compounds having valuable properties, in particular those which can be used for the preparation of medicaments.

It has been found that the compounds of the formula I and salts thereof have very valuable pharmacological properties while being well tolerated. They exhibit SGLT1- and SGLT2- (sodium dependent glucose co-transporter) inhibiting properties and can therefore be employed for combating and preventing type 1 and type 2 diabetes.

The absorption of glucose in the brush border of the small intestine and the proximal tubules of the kidney against a concentration gradient occurs via epithelial sodium-dependent glucose cotransporters (SGLTs). At least two major classes of SGLTs have been described: SGLT1 (for example Lee W. S. et al. (1994) The high-affinity Na+/Glucose co-transporter: reevaluation of function and distribution of expression. J. Biol. Chem. 269, 12032-12039) and SGLT2 (for example Mackenzie B. et al. (1994) SAAT1 is a low-affinity Na+/glucose cotransporter and not an amino acid transporter. J. Biol. Chem. 269, 22488-22491).

SGLT1 is thought to be important for the absorption of glucose in the gut, whereas SGLT2 is probably primarily responsible for the re-absorption of freely filtered glucose in the kidney.

The major change in diabetes mellitus is hyperglycaemia. This is not only a symptom of the disease, but also a potential pathogenic factor leading to multiple chronic diabetic microand macrovascular complications and an impairment of insulin secretion and sensitivity (Klein R. (1995), Hyperglycemia and microvascular and macrovascular disease in diabetes, Diabetes Care 18, 258-268; Rossetti L. (1995), Glucose toxicity: the implications of hyperglycemia in the pathophysiology of diabetes mellitus, Clin. Invest. Med. 18, 255-260). Thus, an important therapeutic aim in the case of the diabetes patient is exclusive regulation of the blood glucose levels within the normal range. In accordance with their described function, inhibition of SGLTs results in reduced absorption and increased excretion of glucose, and a subsequent decrease in blood glucose levels. Thus, suppression of SGLTs may be a suitable alternative for the treatment of diabetes.

The literature describes a number of classes of substance having an SGLT action. The model for all these structures was the natural product phlorizin. Aromatic glycoside derivatives are known from WO 2004/052902 and WO 2004/052903. Propiophenone glycosides are described in WO 0280936, WO 0280935, JP 2000080041 and EP 850948. Glucopyranosyloxybenzylbenzenes are described in WO 0244192, WO 0228872 and WO 0168660. Glucopyranosyloxypyrazoles are known from WO 0268440, WO 0268439, WO 0236602 and WO 0116147. O-glycoside benzamides are disclosed in WO 0174835 and WO 0174834. C-arylglycosides are described in WO 0127128 and US 2002137903. All known structures contain the glucose as a very important structural element. Furthermore, US 2002/132807 discloses diaryl sulfide compounds for the treatment of inflammatory and immune diseases. EP 0 953 357 A1 describes in general glycoside compounds as renal drug carriers, and WO 95/23780 describes 4-hydroxyphenoxyheterocycloalkyl compounds as skin lighteners.

The compounds according to the invention have high splitting with respect to the desired affinity from $SGLT_2$ to $SGLT_1$.

The compounds of the formula I are distinguished by favourable actions on glucose metabolism, in particular they lower the blood sugar level and are suitable for the treatment of type 1 and type 2 diabetes. The compounds can therefore be employed alone or in combination with further blood sugar-lowering active compounds (antidiabetics).

The compounds of the formula I are furthermore suitable for the prevention and treatment of late damage in diabetes, such as, for example, nephropathy, retinopathy, neuropathy and syndrome X, obesity, cardiac infarction, myocardial infarction, peripheral arterial occlusion diseases, thromboses, arteriosclerosis, inflammation, immune diseases, autoimmune diseases, such as, for example, AIDS, asthma, osteoporosis, cancer, psoriasis, Alzheimer's, schizophrenia and infectious diseases, preferably the treatment of type 1 and type 2 diabetes and for the prevention and treatment 15 of late damage in diabetes, syndrome X and obesity.

The compounds of the formula I can be employed as medicament active compounds in human and veterinary medicine, in particular for the treatment and prevention of type 1 and type 2 diabetes.

The invention relates to the compounds of the formula I and salts thereof and to a process for the preparation of compounds of the formula I and pharmaceutically usable salts and stereoisomers thereof, characterised in that
a) a compound of the formula II

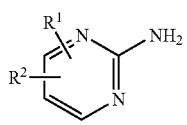

II in which
$R^1$ and $R^1$ have the meanings indicated in claim 1, is reacted with a compound of the formula III

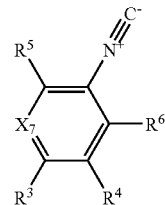

III in which
$R^3$, $R^4$, $R^5$, $R^6$ and $X_7$ have the meanings indicated in claim 1,
and with a compound of the formula IV $$O=CH-W-T \qquad IV$$

in which W and T have the meanings indicated in claim 1,
or
b) a radical T is converted into another radical T
   by cyclising a thiosemicarbazide derivative to give an oxadiazole derivative,
and/or
a base or acid of the formula I is converted into one of its salts.

The invention also relates to the optically active forms (stereoisomers), the enantiomers, the racemates, the diastereomers and the hydrates and solvates of these compounds. "Solvate of the compounds" are taken to mean adductions of inert solvent molecules onto the compounds which form owing to their mutual attractive force. Solvates are, for example, mono- or dihydrates or alcoholates.

The compounds of the formula I also mean pharmaceutically usable derivatives and solvates thereof.

"Pharmaceutically usable derivatives" are taken to mean, for example, the salts of the compounds according to the invention and also so-called prodrug compounds.

"Prodrug derivatives" are taken to mean compounds of the formula I which have been modified with, for example, alkyl or acyl groups, sugars or oligopeptides and which are rapidly cleaved in the organism to form the active compounds according to the invention.

These also include biodegradable polymer derivatives of the compounds according to the invention, as described, for example, in Int. J. Pharm. 115, 61-67 (1995).

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The compounds according to the invention may also be in various polymorphic forms, for example as amorphous and crystalline polymorphic forms. All polymorphic forms of the compounds according to the invention belong within the scope of the invention and are a further aspect of the invention.

For all radicals which occur more than once, their meanings are independent of one another.

Above and below, the radicals or parameters W, T, $R^1$, $R^2$, $R^3$, $R^4$, $R^5$ and $R^6$ have the meanings indicated under the formula I, unless expressly indicated otherwise.

A, A', A" preferably denote, in each case independently of one another, alkyl, is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl.

A, A', A" very particularly preferably denote, in each case independently of one another, alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Cyclic alkyl or cycloalkyl preferably denotes cyclopropyl, cyclobutyl, cylopentyl, cyclohexyl or cycloheptyl.

$R^1$, $R^2$ preferably denote, in each case independently of one another, H or A.

$R^1$, $R^2$ particularly preferably denote, in each case independently of one another, H or methyl.

$R^3$, $R^4$ preferably denote, in each case independently of one another, H, F, Cl, methyl, $CF_3$ or methoxy.

$R^5$, $R^6$ preferably denote, in each case independently of one another, Hal, methyl, ethyl, isopropyl, $CF_3$ or methoxy.

Irrespective of further substitutions, Het denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzo-thiadiazol-4- or -5-yl or 2,1,3-benzoxadiazol-5-yl.

The heterocyclic radicals may also be partially hydrogenated.

Het may thus also denote, for example, 2,3-dihydro-2-, -3-, -4- or -5-furyl, 2,5-dihydro-2-, -3-, -4- or 5-furyl, 2,3-dihydro-1-, -2-, -3-, -4- or -5-pyrrolyl, 2,5-dihydro-1-, -2-, -3-, -4- or -5-pyrrolyl, 2,3-dihydro-1-, -2-, -3-, -4- or -5-pyrazolyl, 1,4-dihydro-1-, -2-, -3- or -4-pyridyl, 1,2,3,4-tetrahydra-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl.

The aromatic or unsaturated ring systems may preferably be mono-, di- or trisubstituted by A, Hal, OA, OH, SA, NAA', SOA, $SO_2A$, $NO_2$, CN, COOA, COOH, CHO, COA, $SO_3HOCOA$, CONAA', NA'COA, NACONA'A", NA'$SO_2$A, $SO_2$NAA', =S, =$NR^1$ and/or =O (carbonyl oxygen).

Het particularly preferably denotes a monocyclic saturated, unsaturated or aromatic heterocycle having 1 to 4 N, O and/or S atoms, which may be mono-, di- or trisubstituted by A, Hal, OA, OH, $NH_2$, NHA, NAA' and/or =O (carbonyl oxygen).

Het very particularly preferably denotes fury/, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl or pyrazinyl, each of which is unsubstituted or mono- or disubstituted by A, Hal, OA, OH, $NH_2$, NHA, NAA' and/or =O (carbonyl oxygen).

Hal preferably denotes F, Cl or Br, but also I.

m preferably denotes 1 or 2.

The compounds of the formula I can have one or more chiral centres and therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to Ik, which conform to the formula I and in which the radicals not designated in greater detail have the meaning indicated under the formula I, but in which in Ia A, A', A" each, independently of one another, denotes unbranched or branched alkyl having 1, 2, 3, 4, 5 or 6 C atoms, in which 1-5H atoms may be replaced by F, or cycloalkyl having 3-7 C atoms;

in Ib $R^1$, $R^2$ each, independently of one another, denote H or A;

in Ic $R^3$, $R^4$ each, independently of one another, denote H, F, Cl, methyl, $CF_3$ or methoxy;

in Id $R^5$, $R^6$ each, independently of one another, denote Hal, methyl, ethyl, isopropyl, $CF_3$ or methoxy;

in Ie

W denotes

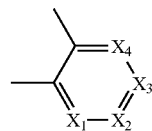

$X_1$ denotes CH, C-methyl, C-ethyl, C—$OCH_3$ or CHal, $X_2$ denotes CH, $X_3$ denotes CH, CHal or C—$OCH_3$, $X_4$ denotes CH;

in If T denotes Het, COOR, CONRR', CONRNRR', CONROR' (hydroxamic acid) or $O(CH_2)_m CONRR'$;

in Ig Het denotes a monocyclic unsaturated or aromatic heterocycle having 1 to 4 N, O and/or S atoms, which may be mono-, di- or trisubstituted by A, Hal, OA, OH, $NH_2$, NHA, NAA' and/or =O (carbonyl oxygen);

in Ih R, R' each, independently of one another, denote H or linear or branched alkyl having 1-6 C atoms, in which 1-5H atoms may be replaced by F and/or Cl;

in Ii R, R' denote H;

in Ij Het denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl or pyrazinyl, each of which is unsubstituted or mono- or disubstituted by A, Hal, OA, OH, $NH_2$, NHA, NAA' and/or =O (carbonyl oxygen);

in Ik

W denotes

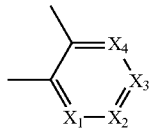

$X_1$ denotes CH, C-methyl, C-ethyl, C—OCH$_3$ or CHal,
$X_2$ denotes CH,
$X_3$ denotes CH, CHal or C—OCH$_3$,
$X_4$ denotes CH,
$X_7$ denotes CH,
$R^1$, $R^2$ each, independently of one another, denote H or A,
$R^3$, $R^4$ each, independently of one another, denote H, F, Cl, methyl, CF$_3$ or methoxy,
$R^5$, $R^6$ each, independently of one another, denote Hal, methyl, ethyl, isopropyl, CF$_3$ or methoxy,
A, A' each, independently of one another, denote unbranched or branched alkyl having 1, 2, 3, 4, 5 or 6 C atoms, in which 1-5H atoms may be replaced by F, or cycloalkyl having 3-7 C atoms,
T denotes Het, COOR, CONRR', CONRNRR', CONROR' or O(CH$_2$)$_m$CONRR',
R, R' each, independently of one another, denote H or linear or branched alkyl having 1-6 C atoms, in which 1-5H atoms may be replaced by F and/or Cl,
Het denotes a monocyclic unsaturated or aromatic heterocycle having 1 to 4 N, O and/or S atoms, which may be mono-, di- or trisubstituted by A, Hal, OA, OH, NH$_2$, NHA, NAA' and/or =O (carbonyl oxygen);
and pharmaceutically usable salts and stereoisomers thereof, including mixtures thereof in all ratios.

In addition, the compounds of the formula I and also the starting materials for their preparation are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use may also be made here of variants known per se which are not mentioned here in greater detail.

If desired, the starting materials can also be formed in situ by not isolating them from the reaction mixture, but instead immediately converting them further into the compounds of the formula I.

The starting compounds of the formulae II, III and IV are generally known. If they are novel, however, they can be prepared by methods known per se.

Compounds of the formula I can preferably be obtained by reacting compounds of the formula II with compounds of the formula III and IV. The reaction is carried out analogously to H. Bienaymé et al., Angew. Chem. 1998, 110, 2349.

The reaction is generally carried out in an inert solvent, in the presence of an activating agant, preferably perchioric acid.

Depending on the conditions used, the reaction time is between a few minutes and 14 days, the reaction temperature is between about 0° and 150°, normally between 5° and 90°, particularly preferably between 10° and 70° C.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane (DCM); alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents; ethanol is particularly preferred.

The aldehydes of the formula IV are accessible, for example, by cross-coupling reactions, such as the Suzuki reaction, from corresponding boronic acids and Het bromides (for example A. Furstner, V. Manabe, JOC 2002, 67, 6264-6267).

Compounds of the formula I can furthermore be obtained by cyclising a thiosemicarbazide derivative to give an oxadiazole derivative.

The reaction is generally carried out in an inert solvent, such as, for example, methanol, preferably in the presence of mercury(II) acetate.

Depending on the conditions used, the reaction time is between a few minutes and 14 days, the reaction temperature is between about 0° and 150°, normally between 5° and 90°, particularly preferably between 10° and 100° C.

5-Amino-1,3,4-oxadiazol-2-yl derivatives can furthermore be obtained by reacting a benzohydrazide derivative with cyanogen bromide. The reaction is preferably carried out in water in the presence of, for example, sodium hydrogencarbonate. Depending on the conditions used, the reaction time is between a few minutes and 14 days, the reaction temperature is between about 0° and 150°, normally between 5° and 90°, particularly preferably between 10° and 100° C.

Pharmaceutical Salts and Other Forms

The said compounds of the formula I can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds of the formula I include aluminium, ammonium, calcium, copper, iron (III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamino resins, procaine, purines, theobromine, triethanolamine, triethylamine, trimethylamine, tripropylamine and tris(hydroxymethyl)methylamine (tromethamine), but this is not intended to represent a restriction.

Compounds of the formula I of the present invention which contain basic nitrogen-containing groups can be quaternised using agents such as $(C_1-C_4)$ alkyl halides, for example methyl, ethyl, isopropyl and Cert-butyl chloride, bromide and iodide; di($C_1-C_4$)alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl($C_1-C_4$)alkyl halides, for example benzyl chloride and phenethyl bromide. Both water- and oil-soluble compounds of the formula I can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds of the formula I are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound of the formula I contains more than one group which is capable of forming pharmaceutically acceptable salts of this type, the formula I also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active compound which comprises a compound of the formula I in the form of one of its salts, in particular if this salt form imparts improved pharmacokinetic properties on the active compound compared with the free form of the active compound or any other salt form of the active compound used earlier. The pharmaceutically acceptable salt form of the active compound can also provide this active compound for the first time with a desired pharmacokinetic property which it did not have earlier and can even have a positive influence on the pharmacodynamics of this active compound with respect to its therapeutic efficacy in the body.

Owing to their molecular structure, compounds of the formula I according to the invention can be chiral and can accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of the compounds of the formula I and/or physiologically acceptable salts thereof for the preparation of a medicament (pharmaceutical composition), in particular by non-chemical methods. In this case, they can be converted into a suitable dosage form together with at least one solid, liquid and/or semi-liquid excipient or adjuvant and optionally in combination with one or more further active compounds.

The invention furthermore relates to medicaments comprising at least one compound of the formula I and/or pharmaceutically usable salts and stereoisomers thereof, including mixtures thereof in all ratios, and optionally excipients and/or adjuvants.

These compositions can be used as medicaments in human or veterinary medicine.

Pharmaceutical formulations can be administered in the form of dosage units which comprise a predetermined amount of active compound per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active compound per dosage unit. Preferred dosage unit formulations are those which comprise a daily dose or part-dose, as indicated above, or a corresponding fraction thereof of an active compound. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active compound with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The active compounds can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compounds. Syrups can be prepared by dissolving the compounds in an aqueous solution with a suitable flavour, while elixirs are prepared using a non-toxic alcoholic vehicle. Suspensions can be formulated by dispersion of the compounds in a non-toxic vehicle, Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and pharmaceutically usable salts thereof and the other active compounds can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and pharmaceutically usable salts thereof and the other active compounds can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsiloncaprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active compound can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active compound can be employed either with a paraffinic or a water-miscible cream base. Alternatively, the active compound can be formulated to give a cream with an oil-in-water cream base or a water-in-oil base.

Pharmaceutical formulations adapted for topical application to the eye include eye drops, in which the active compound is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in the freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I and of the other active compound depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or more usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

The invention furthermore relates to the use of compounds of the formula I, in combination with at least one further medicament active compound, preferably for the treatment of type 1 and type 2 diabetes, in particular for lowering blood sugar.

Suitable further active compounds for the combination preparations are:

All antidiabetics mentioned in the Rote Liste [Red List] 2001, Chapter 12. They can be combined with the compounds of the formula I according to the invention, in particular in order to enhance the action synergistically. The active-ingredient combination can be administered either by administration of the active compounds to the patient separately or in the form of combination preparations which comprise a plurality of active compounds in a single pharmaceutical composition. Most of the active compounds listed below are disclosed in USP Dictionary of USAN and International Drug Names, US Pharmacopeia, Rockville 2001. Antidiabetics include insulin and insulin derivatives, such as, for example, Lantus® (see www.lantus.com) or HMR 1964, fast-acting insulins (see U.S. Pat. No. 6,221,633), GLP-1 derivatives, such as, for example, those disclosed by Novo Nordisk A/S in WO 98/08871, and orally effective hypoglycaemic active compounds.

The orally effective hypoglycaemic active compounds preferably include sulfonylureas, biguanidines, meglitinides, oxadiazolidinediones, thiazolidinediones, glucosidase inhibitors, glucagon antagonists, GLP-1 agonists, potassium channel openers, such as, for example, those disclosed by Novo Nordisk A/S in WO 97/26265 and WO 99/03861, insulin sensitisers, inhibitors of liver enzymes which are involved in the stimulation of gluconeogenesis and/or glycogenolysis, glucose uptake modulators, compounds which modify fat metabolism, such as antihyperlipidaemic active compounds and antilipidaemic active compounds, compounds which reduce the intake of foods, PPAR and PXR agonists, and active compounds which act on the ATP-dependent potassium channel of the beta cells.

In an embodiment of the invention, the compounds of the formula I are administered in combination with an HMGCoA reductase inhibitor, such as simvastatin, fluvastatin, pravastatin, lovastatin, atorvastatin, cerivastatin, rosuvastatin.

In an embodiment of the invention, the compounds of the formula I are administered in combination with a cholesterol absorption inhibitor, such as, for example, ezetimibe, tiqueside, pamaqueside.

In an embodiment of the invention, the compounds of the formula I are administered in combination with a PPAR gamma agonist, such as, for example, rosiglitazone, pioglitazone, JTT-501, GI 262570.

In an embodiment of the invention, the compounds of the formula I are administered in combination with PPAR alpha agonist, such as, for example, GW 9578, GW 7647.

In an embodiment of the invention, the compounds of the formula I are administered in combination with a mixed PPAR alpha/gamma agonist, such as, for example, GW 1536, AVE 8042, AVE 8134, AVE 0847, AVE 0897, or as described in WO 00/64888, WO 00/64876, WO 03/20269.

In an embodiment of the invention, the compounds of the formula I are administered in combination with a fibrate, such as, for example, fenofibrate, clofibrate, bezafibrate.

In an embodiment of the invention, the compounds of the formula I are administered in combination with an MTP inhibitor, such as, for example, implitapide, BMS-201038, R-103757. In an embodiment of the invention, the compounds of the formula I are administered in combination with bile acid absorption inhibitor (see, for example, U.S. Pat. No. 6,245,744 or U.S. Pat. No. 6,221,897), such as, for example, HMR 1741.

In an embodiment of the invention, the compounds of the formula I are administered in combination with a CETP inhibitor, such as, for example, STT-705.

In an embodiment of the invention, the compounds of the formula I are administered in combination with a polymeric bile acid adsorber, such as, for example, cholestyramine, colesevelam.

In an embodiment of the invention, the compounds of the formula I are administered in combination with an LDL receptor inducer (see U.S. Pat. No. 6,342,512), such as, for example, HMR1171, HMR1586.

In an embodiment of the invention, the compounds of the formula I are administered in combination with an ACAT inhibitor, such as, for example, avasimibe.

In an embodiment of the invention, the compounds of the formula I are administered in combination with an antioxidant, such as, for example, OPC-14117.

In an embodiment of the invention, the compounds of the formula I are administered in combination with a lipoprotein lipase inhibitor, such as, for example, NO-1886.

In an embodiment of the invention, the compounds of the formula I are administered in combination with an ATP citrate lyase inhibitor, such as, for example, SB-204990.

In an embodiment of the invention, the compounds of the formula I are administered in combination with a squalene synthetase inhibitor, such as, for example, BMS-188494. In an embodiment of the invention, the compounds of the formula I are administered in combination with a lipoprotein(a) antagonist, such as, for example, CI-1027 or nicotinic acid. In an embodiment of the invention, the compounds of the formula I are administered in combination with a lipase inhibitor, such as, for example, orlistat.

In an embodiment of the invention, the compounds of the formula I are administered in combination with insulin.

In an embodiment, the compounds of the formula I are administered in combination with a sulfonylurea, such as, for example, tolbutamide, glibenclamide, glipizide or glimepiride.

In an embodiment, the compounds of the formula I are administered in combination with a biguanide, such as, for example, metformin.

In another embodiment, the compounds of the formula I are administered in combination with a meglitinide, such as, for example, repaglinide.

In an embodiment, the compounds of the formula I are administered in combination with a thiazolidinedione, such as, for example, troglitazone, ciglitazone, pioglitazone, rosiglitazone or the compounds which are disclosed by Dr. Reddy's Research Foundation in WO 97/41097, in particular 5-[[4-[(3,4-dihydro-3-methyl-4-oxo-2-quinazolinyl-methoxy]phenyl]methyl]-2,4-thiazolidinedione.

In an embodiment, the compounds of the formula I are administered in combination with an α-glucosidase inhibitor, such as, for example, miglitol or acarbose.

In an embodiment, the compounds of the formula I are administered in combination with an active compound which acts on the ATP-dependent potassium channel of the beta cells, such as, for example, tolbutamide, glibenclamide, glipizide, glimepiride or repaglinide.

In an embodiment, the compounds of the formula I are administered in combination with more than one of the above-mentioned compounds, for example in combination with a sulfonylurea and metformin, a sulfonylurea and acarbose, repaglinide and metformin, insulin and a sulfonylurea, insulin and metformin, insulin and troglitazone, insulin and lovastatin, etc.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists, for example naphthalene-1-sulfonic acid {4-[(4-aminoquinazolin-2-ylamino) methyl]cyclohexylmethyl}-amide; hydrochloride (CGP 71683A)), MC4 agonists (for example 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]amide; (WO 01/91752)), orexin antagonists (for example 1-(2-methylbenzoxazol-6-yl)-3-[1,5]naphthyridin-4-ylurea; hydrochlorides (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (for example [2-methyl-9-(2,4,6-trimethylphenyl)-9H-1,3,9-triazafluoren-4-yl]dipropylamine (WO 00/66585)), CRF BP antagonists (for example urocortin), urocortin agonists, β3 agonists (for example 1-(4-chloro-3-methanesulfonylmethylphenyl)-2-[2-(2,3-dimethyl-1H-indol-6-yloxy)ethylamino]ethanol; hydrochlorides (WO 01/83451)), MSH (melanocyte-stimulating hormone) agonists, CCK-A agonists (for example {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)); serotonin reuptake inhibitors (for example dexfenfluramines), mixed serotonin compounds and noradrenergic compounds (for example WO 10 00/71549), 5HT agonists, for example 1-(3-ethylbenzofuran-7-yl)piperazine oxalic acid salt (WO 01/09111), bombesin agonists, galanin antagonists, growth hormone (for example human growth hormone), growth hormone-releasing compounds (tert-butyl 6-benzyloxy-1-(2-diisopropylaminoethylcarbamoyl)-3,4-dihydro-1H-isoquinoline-2-carboxylate (WO 01/85695)), TRH agonists (see, for example, EP 0 462 884) uncoupling protein 2- or 3-modulators, leptin agonists (see, for example, Lee, Daniel W.; Leinung, Matthew C.; Rozhayskaya-Arena, Marina; Grasso, Patricia. Leptin agonists as a potential approach to the treatment of obesity, Drugs of the Future (2001), 26(9), 873-881), DA agonists (bromocriptine, doprexin), lipase/amylase inhibitors (for example WO 00/40569), PPAR modulators (for example WO 00/78312), RXR modulators or TR-β agonists.

In an embodiment of the invention, the additional active compound is leptin; see, for example, "Perspectives in the therapeutic use of leptin", Salvador, Javier; Gomez Ambrosi, Javier; Fruhbeck, Gema, Expert Opinion on Pharmacotherapy (2001), 2(10), 1615-1622.

In an embodiment, the additional active compound is dex-amphatamine or amphetamine.

In an embodiment, the additional active compound is fenfluramine or dexfenfluramine.

In yet another embodiment, the additional active compound is sibutramine.

In an embodiment, the additional active compound is orlistat.

In an embodiment, the additional active compound is mazindol or phentermine.

In an embodiment, the compounds of the formula I are administered in combination with roughage, preferably insoluble roughage (see, for example, Carob/Caromax® (Zunft H J; et al., Carob pulp preparation for treatment of hypercholesterolemia, ADVANCES IN THERAPY (2001 September-October), 18(5), 230-6.) Caromax is a carob-containing product from Nutrinova, Nutrition Specialties & Food Ingredients GmbH, Industriepark Höchst, 65926 Frankfurt/Main)). The combination with Caromax® can be effected in a single composition or by administration of compounds of the formula I and Caromax® separately. In this connection, Caromax® can also be administered in the form of foods, such as, for example, in bakery products or muesli bars.

It goes without saying that each suitable combination of the compounds according to the invention with one or more of the above-mentioned compounds and optionally one or more further pharmacologically active substances is regarded as falling within the scope of protection of the present invention.

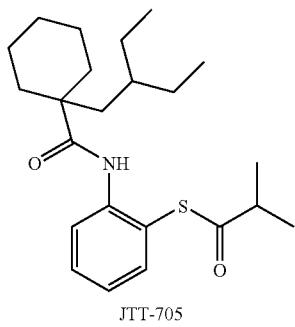

JTT-705

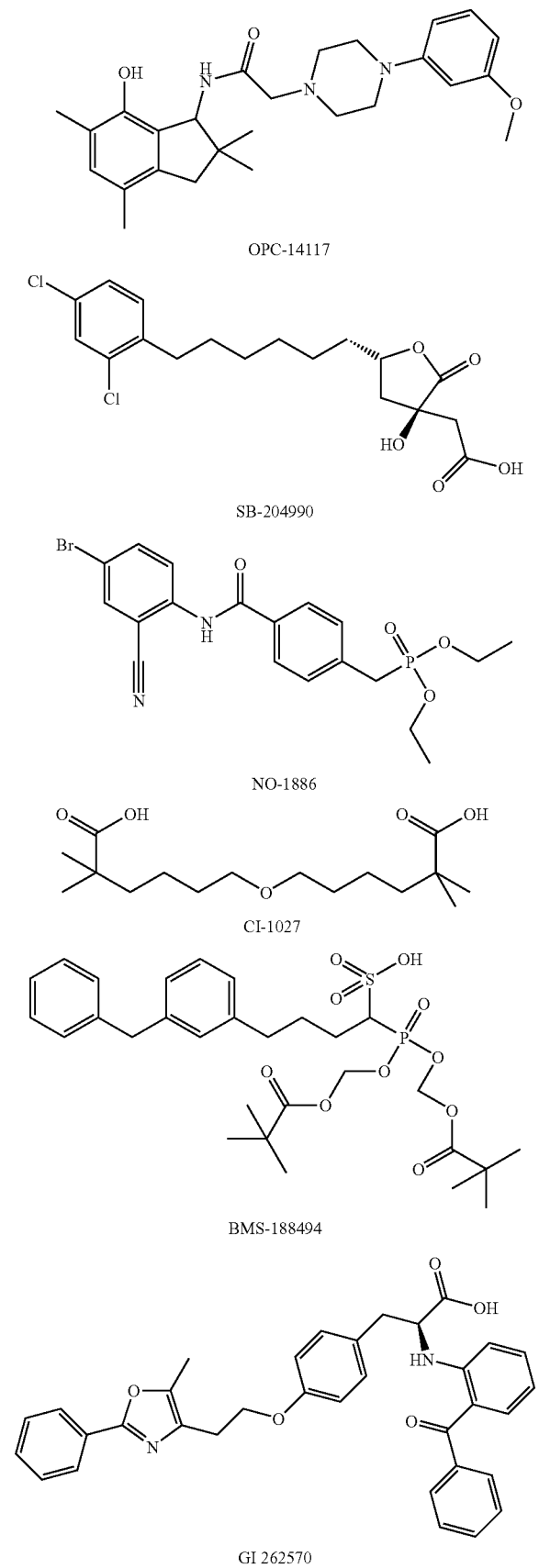

-continued

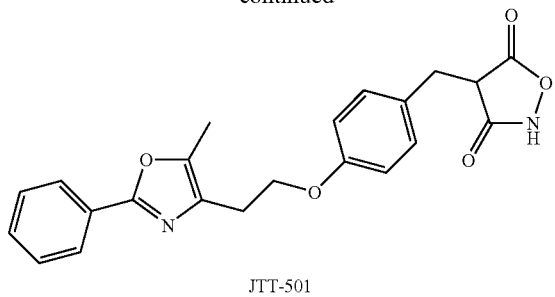

JTT-501

The invention also relates to a set (kit) consisting of separate packs of
(a) an effective amount of a compound of the formula I and/or pharmaceutically usable salts and stereoisomers thereof, including mixtures thereof in all ratios, and
(b) an effective amount of a further medicament active compound.

The set comprises suitable containers, such as boxes, individual bottles, bags or ampoules. The set may, for example, comprise separate ampoules, each containing an effective amount of a compound of the formula I and/or pharmaceutically usable salts and stereoisomers thereof, including mixtures thereof in all ratios,
and an effective amount of a further medicament active compound in dissolved or lyophilised form.

The compounds can be tested for their SGLT inhibition properties by means of BHK cells expressing SGLT1 and SGLT2. The production of the cells and the testing can be carried out as described below.

Construction and Expression of SGLT1 in BHK Cells

To construct the SGLT1 expression vector (KL225), the SLC5A1 gene (homologous to NM_000343) was amplified from a cDNA library using standard PCR technology and cloned over NheI/XhoI sites into the pcDNA3.1 expression vector (Invitrogen) containing neomycin as a selection marker. In this vector, transcription uses the enhancer/promoter of human cytomegalovirus.

The final vector KL225 together with an additional vector containing a dihydrofolate reductase gene as a selection marker was introduced into cells. Transfection into BHK21 cells (ATCC CCL-10), cultivated in DMEM medium (GIBCO/BRL), supplemented with 10% foetal calf serum (FCS) and 20 mM glutamine, was carried out using calcium phosphate transfections according to Graham, F. L. and van der Ebb, A. J. (1973), Virology 52: 456 with 5-20 µg of uncut plasmids for $10^7$ cells. Stable transfectants were selected in medium containing 1 mg/ml of G418 (GIBCO/BRL) and 20-5000 nM methotrexate as final concentration, where only cells which expressed the neomycin gene and overexpressed the dhfr gene were able to grow. After growth for 2-3 weeks, the cells were cloned (0.5 cells/well) and the clones were investigated for SGLT expression in radioactivity uptake tests.

Construction and Expression of SGLT2 in BHK Cells

To construct the SGLT2 expression vector (KL224), the SLC5A2 gene (homologous to NM_003041) was amplified from a cDNA library using standard PCR technology and cloned over NheI/XhoI sites into PCI-neo expression vector (Promega) containing neomycin as a selection marker. In this vector, transcription uses the enhancer/promoter of human cytomegalovirus and the SV40 polyadenylation signal.

The final vector KL224 together with an additional vector containing a dihydrofolate reductase gene as a selection marker was introduced into cells. Transfection into BHK21 cells (ATCC CCL-10), cultivated in DMEM medium (GIBCO/BRL), supplemented with 10% foetal calf serum (FCS) and 20 mM glutamine, was carried out using calcium phosphate transfections according to Graham, F. L. and van der Ebb, A. J. (1973), Virology 52: 456 with 5-20 µg of uncut plasmids for $10^7$ cells. Stable transfectants were selected in medium containing 1 mg/ml of G418 (GIBCO/BRL) and 20-5000 nM methotrexate as final concentration, where only cells which expressed the neomycin gene and overexpressed the dhfr gene were able to grow. After growth for 2-3 weeks, the cells were cloned (0.5 cells/well) and the clones were investigated for SGLT expression in radioactivity uptake tests.

Method of SGLT1/2 Activity Measurement

The uptake of $^{14}$C-α-methyl-D-glucopyranoside (AMG) in, for example, Xenopus oocytes injected with the corresponding cRNA has been described in principle (for example Wen-Sen Lee et al. (1994), J. Biol. Chem. 269, 12032-12039; Guofeng You et al. (1995), J. Biol. Chem. 270, 29365-29371).

A 96-well cell-based assay was developed and adapted to HTS requirements:

BHK cells (transfected with SGLT1 or SGLT2) were seeded into 96-well microtitre plates (Cultureplates, Perkin Elmer). After at least 24 h, medium was removed, and the cell layer was washed with assay buffer (140 mM NaCl, 2 mM KCl, 1 mM $CaCl_2$, 1 mM $MgCl_2$, 10 mM HEPES, 5 mM Tris, adjusted to pH 7.4 using 1 M KOH). After addition of 40 µl of assay buffer, 50 µl of AMG (50 µM for SGLT1 and 2 mM for SGLT2) in the presence or absence of compounds, the cells were incubated in a total volume of 100 µl at 37° C. for 90 min. Supernatant was removed by suction and discarded. Cells were washed and lysed by addition of 50 µl of water. After 10 min at room temperature, 200 µl of Micrsoscint 40 (Perkin Elmer) were added. The radioactivity was counted in a Topcount microplate scintillation counter (Perkin Elmer). The non-specific uptake was determined in sodium-free assay buffer (266 mM sucrose, 2 mM KCl, 1 mM $CaCl_2$, 1 mM $MgCl_2$, 10 mM HEPES, 5 mM Tris, adjusted to pH 7.4 using 1 M KOH).

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent: ethyl acetate/methanol 9:1.

Mass spectrometry (MS): EI (electron impact ionisation) $M^+$

FAB (fast atom bombardment) $(M+H)^+$

ESI (electrospray ionisation) $(M+H)^+$ (unless indicated otherwise)

HPLC Method

Hewlett Packard HP 1100 series system having the following features: ion source: electrospray (positive mode); scan: 100-1000 m/e; fragmentation voltage: 60 V; gas temperature: 300° C., DAD: 220 nm.

Flow rate: 2.4 ml/min. The splitter used reduced the flow rate for MS after the DAD to 0.75 ml/min.

Column: Chromolith SpeedROD RP-18e 50-4.6
Solvent: LiChrosolv grade from Merck KGaA
Solvent A: $H_2O$ (0.01% of TFA)
Solvent B: $CH_3CN$ (0.008% of TFA)
Column: Chromolith SpeedROD RP-18e 50-4.6

Solvent: LiChrosolv grade from Merck KGaA
Solvent A: H$_2$O (0.01% of TFA)
Solvent B: CH$_3$CN (0.008% of TFA)
Gradient:
20% of B 100% of B: 0 min to 2.8 min
100% of B: 2.8 min to 3.3 min
100% of B 20% of B: 3.3 min to 4 min
Gradient for "polar" condition
5% of B 100% of B: 0 min to 3 min
100% of B: 3 min to 3.5 min
100% of B 5% of B: 3.5 min to 3.6 min

EXAMPLE 1

The preparation of 2-{2-[3-(2,6-dimethylphenylamino) imidazo[1,2-a]-pyrimidin-2-yl]-3-ethylphenoxy}acetamide ("A8") is carried out analogously to the following scheme:

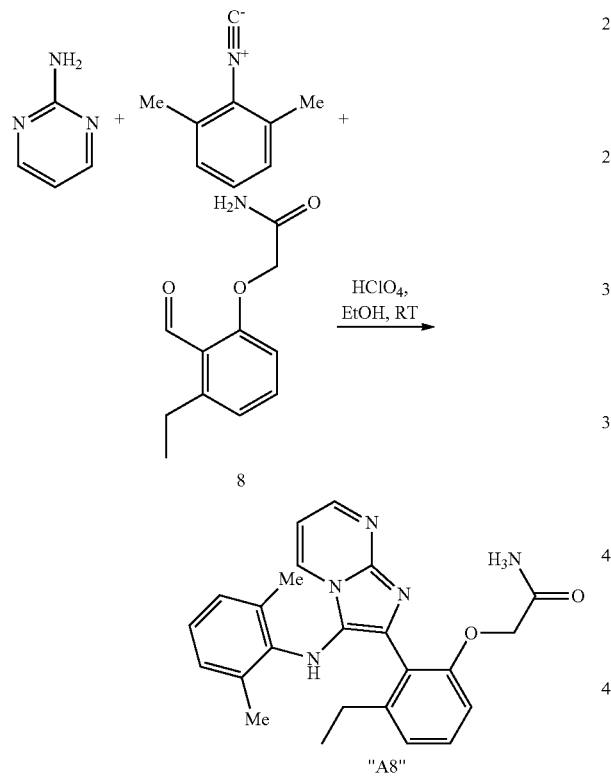

Analogously to H. Bienaymé et al. *Angew. Chem.* 1998, 1002349:

0.51 g (5.36 mmol) of 2-aminopyrimidine and 1.0 g (4.83 mmol) of aldehyde 8 is dissolved successively in 70 ml of ethanol at RT under inert gas. 0.7 g (5.36 mmol) of 2,6-dimethylphenyl isocyanide are then added, 0.23 ml of 70% perchloric acid are added dropwise, and the mixture is stirred at RT for a further 20 h. The mixture is subsequently subjected to conventional work-up. Two isomers having the same masses are formed in this reaction. Purification by column chromatography on silica gel gives 1.229 g (55%) of the desired product "A8" as solid, m.p. 130°; MS-FAB (M+H$^+$)= 416.49;

$^1$H-NMR (DMSO-d$_6$) δ [ppm] 8.56 (s, 1H), 8.34 (s, 1H), 7.39 (d, J=13.9 Hz, 1H), 7.23 (t, J=8.01 Hz, 1H), 7.15 (s, 1H), 7.05 (s, 1H), 6.89 (d, J=7.67 Hz, 1H), 6.80 (d, J=7.45 Hz, 2H), 6.70 (d, J=7.44 Hz, 1H), 6.66 (d, J=8.36 Hz, 1H), 4.34 (s, 2H), 2.54-2.40 (m, 2H), 1.84 (s, 6H), 1.05 (t, J=7.53 Hz, 3H).

The starting aldehyde 8 is accessible by the following reaction sequence.

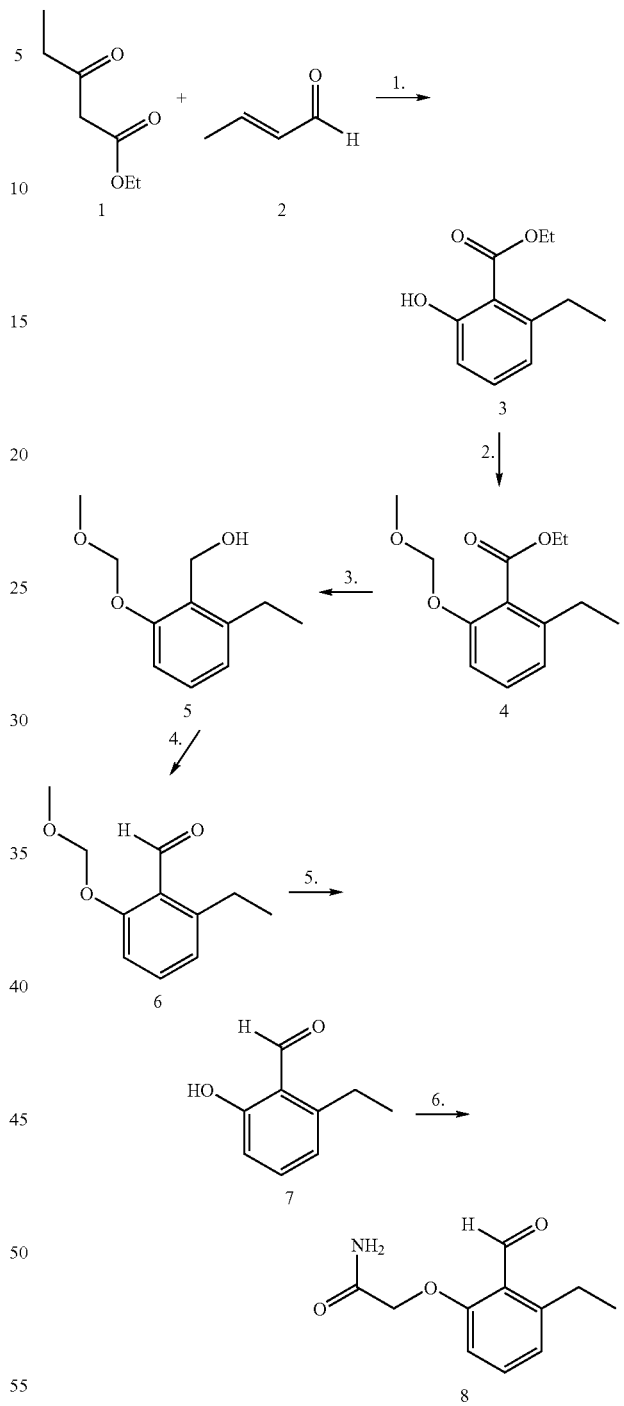

1. By the method of G. Appendino et al. J. Nat. Prod. 1999, 62, 1627: 0.46 g (0.02 mol) of sodium is dissolved in 100 ml of ethanol, and 70.8 ml of ethyl acetate 1 are subsequently added. 50.0 g (0.56 mol) of trans-pentenal 2 is then added dropwise over the course of 5 minutes at 0° C. The reaction mixture is allowed to come to room temperature and is stirred for a further 48 hours. After cooling to 0° C., 50 g of HCl gas are passed in, and the mixture is stirred for a further 48 hours. Excess gas and solvent are removed in vacuo, the residue is dissolved in DMF and heated to 90° C. At this temperature, 33.9 g (0.8 mol) of LiCl and 80.67 g (0.6 mol) of Cu(II) chloride are added, and the mixture is stirred for a further 3 hours. After cooling, the mixture is subsequently subjected to conventional work-up, giving 44 g (40%) of ethyl ester 3 as oil.

2. 44.0 g (0.22 mol) of ethyl ester 3 is dissolved in 500 ml of DMF at room temperature, and 9.2 g (0.23 mol) of sodium hydride suspension is then introduced in small portions. After 1 hour, 20.1 g (0.25 mol) of chloromethyl methyl ether is added dropwise, and the mixture is stirred for 16 h. After cooling, the mixture is subsequently subjected to conventional workup, giving 54 g (100%) of MOM ether 4 as oil.

3. 8.73 g (0.23 mol) of lithium aluminium hydride powder are suspended in 200 ml of THF. 54.0 g (0.22 mol) of MOM ether 4 in 300 ml of THF are subsequently slowly added dropwise at 5-10° C. After stirring at room temperature for 16 h, the mixture is subjected to conventional work-up, giving 50 g (100%) of benzyl alcohol 6 as oil.

4. 50.0 g (0.22 mol) of alcohol 5 is dissolved in 500 ml of chloroform, and 250.0 g (2.87 mol) of manganese(IV) oxide is added in portions. The mixture is subsequently stirred under reflux for 16 h. The mixture is subjected to conventional work-up, giving 16.0 g (41%) of aldehyde 6 as oil.

5. 8.2 g (42 mmol) of aldehyde 6 are dissolved in 100 ml of dioxane/water (1:1), 0.52 g (3.0 mmol) of toluene-4-sulfonic acid monohydrate is added, and the mixture is stirred under reflux for 12 hours. The mixture is subjected to conventional work-up, giving 7.0 g (100%) of phenol 7 as oil.

6. 6.2 g (55 mmol) of potassium tert-butoxide is added in portions with ice-cooling to a solution of 7.0 g (42 mmol) of phenol 7 in 50 ml of DMF, and the mixture is stirred for a further 1 hour. 10.2 g (55 mmol) of 2-iodoacetamide are then slowly added, and the mixture is stirred at room temperature for 16 h. The mixture is subjected to conventional work-up, giving 5.7 g (65%) of oxoacetamide 8 as crystals, m.p. 118-119° C.

The following compounds are obtained analogously to Example 1

| No. | Structure and/or name | MS-FAB (M⁺) | HPLC (polar) R$_f$[min] |
|---|---|---|---|
| "A1" | 2-{2-[3-(2,6-Dimethylphenylamino)-imidazo[1,2-a]pyrimidin-2-yl]phenoxy}-acetamide | 388.44 | |
| "A2" | 2-{2-[3-(2,6-Dimethylphenylamino)-5,7-dimethylimidazo[1,2-a]pyrimidin-2-yl]-phenoxyacetamide | 416.49 | |
| "A7" | 2-{2-[3-(2,6-Dichlorophenylamino)-imidazo[1,2-a]pyrimidin-2-yl]-3-ethyl-phenoxylacetamide | 457.33 | |

-continued

| No. | Structure and/or name | MS-FAB (M+) | HPLC (polar) $R_f$ [min] |
|---|---|---|---|
| | Melting point: 218° C. (decomposition); MS-EI (M+) = 456; <br> $^1$H—NMR (DMSO-$d_6$) δ [ppm] 8.73 (dd, J = 2.00 and 6.76 Hz, 1H), 8.56 (dd, J = 2.00 and 4.12 Hz, 1H), 7.38 (s, 1H), 7.30 (s, 1H), 7.17 (dd, J = 2.90 and 4.08 Hz, 1H), 7.14 (t, J = 7.94 Hz, 1H), 7.11 (d, J = 8.03 Hz, 2H), 6.78 (d, J = 7.63 Hz, 1H), 6.73 (t, J = 8.03 Hz, 1H), 6.63 (d, J = 8.17 Hz, 1H), 4.26 (d, J = 8.98 Hz, 2H), 2.49-2.39 (m, 2H), 2.05 (s, 6H), 0.96 (t, J = 7.54 Hz, 3H). | | |
| "A9" | 2-{2-[3-(2,6-Dimethylphenylamino)-imidazo[1,2-a]pyrimidin-2-yl]-ethyl-5-methoxyphenoxy}acetamide | 446.52 | 1.73 |
| "A10" | 2-{2-[3-(2,6-Dimethylphenylamino)-imidazo[1,2-a]pyrimidin-2-yl]-5-methoxy-3-methylphenoxy}acetamide | 432.49 | 1.60 |
| "A12" | 2-{2-[3-(2,6-Dichlorophenylamino)-imidazo[1,2-a]pyrimidin-2-yl]-3-ethyl-5-methoxyphenoxy}acetamide | 487.36 | 1.69 |
| "A20" | 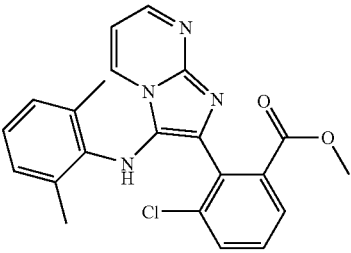 <br> Methyl 3-chloro-2-[3-(2,6-dimethylphenylamino)imidazo[1,2-a]pyrimidin-2-yl)benzoate | 407.87 | 1.83 |

EXAMPLE 2

The preparation of 2-[3-(2,6-dichlorophenylamino)imidazo[1,2-a]pyrimidin-2-yl]-3,5,4-trimethoxybenzamide ("A17") is carried out analogously to the following scheme:

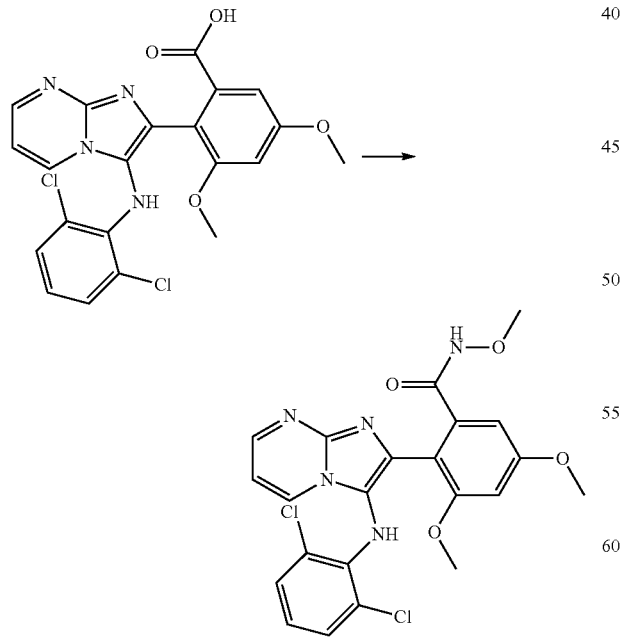

400 mg of 2-[3-(2,6-dichlorophenylamino)imidazo[1,2-a]pyrimidin-2-yl]-3,5-dimethoxybenzoic acid, 73 mg of O-methylhydroxylamine hydrochloride, 200 mg of DAPECI and 88 mg of 4-methylmorpholine are dissolved in 1 ml of DMF and stirred at RT for 1 hour. The solvent is removed, and the residue is purified by column chromatography (heptane/ethyl acetate), giving 90 mg (21%) of 2-[3-(2,6-dichlorophenylamino)imidazo[1,2-a]pyrimidin-2-yl]-N-ethyl-3,5-dimethoxybenzamide (A17) as solid; MS-FAB (M+H+) 489.7; $R_f$ (polar method): 1.61 min.

The compound 2-[3-(2,6-dichloro-3-methylphenylamino)imidazo[1,2-a]-pyrimidin-2-yl]-N-ethyl-3,5-dimethoxybenzamide ("A24") is obtained analogously using ethylamine instead of O-methylhydroxylamine hydrochloride

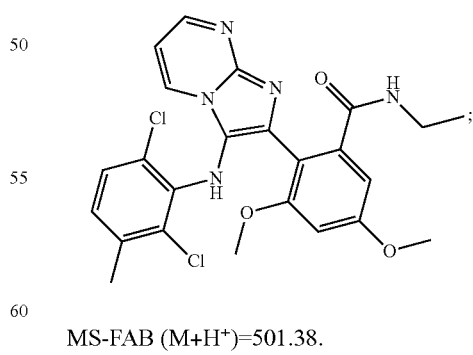

MS-FAB (M+H+)=501.38.

EXAMPLE 3

The preparation of 2-[3-(2,6-dichlorophenylamino)imidazo[1,2-a]pyrimidin-2-yl]-3,5-dimethoxybenzohydrazide ("A18") is carried out analogously to the following scheme:

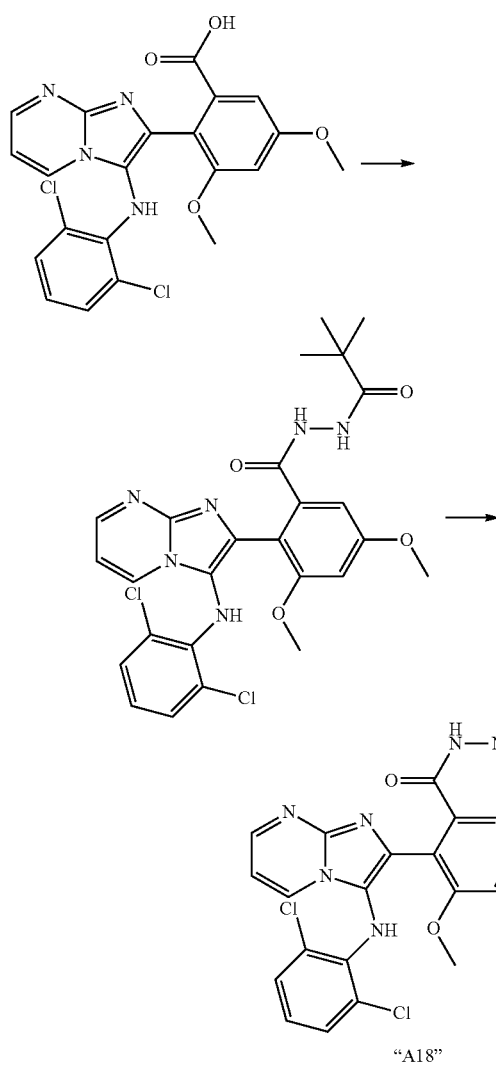

"A18"

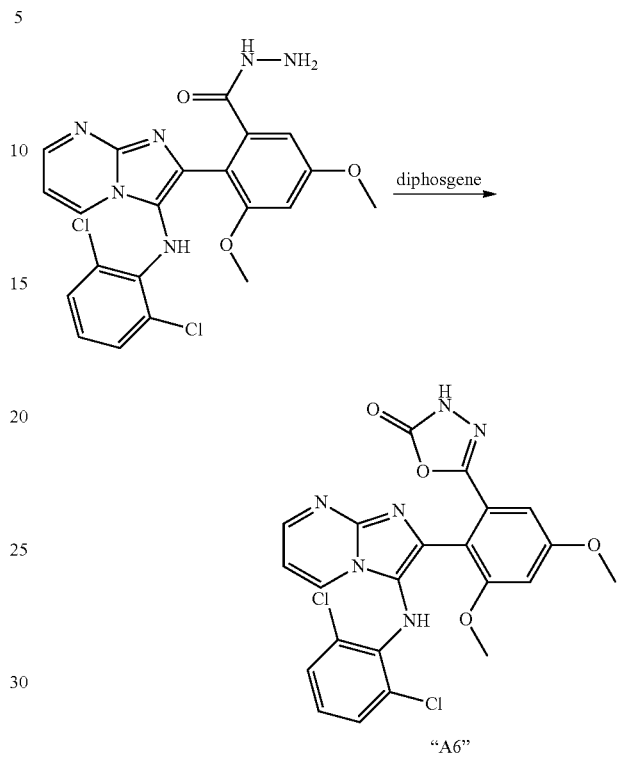

"A6"

3.1 500 mg of 2-[3-(2,6-dichlorophenylamino)imidazo[1,2-a]pyrimidin-2-yl]-3,5-dimethoxybenzoic acid, 144 mg of tert-butyl carbazate and 250 mg of DAPECl are dissolved in 1 ml of DMF and stirred at RT for 16 h. The reaction mixture is poured into water, the precipitate formed is filtered off and dried. Purification by column chromatography (ethyl acetate/methanol) gives 120 mg (19%) of tert-butyl N'-{2-[3-(2,6-dichlorophenylamino)-imidazo[1,2-a]pyrimidin-2-yl]-3,5-dimethoxybenzoyl}hydrazinecarboxylate as solid; MS-FAB (M+H$^+$)=574.2; $R_f$ (polar method): 1.80 min.

3.2 120 mg of tert-butyl N'-{2-[3-(2,6-dichlorophenylamino)imidazo[1,2-a]-pyrimidin-2-yl]-3,5-dimethoxybenzoyl}hydrazinecarboxylate are stirred at RT for 1 hour in 3 ml of 4 N HCl in dioxane. The reaction mixture is evaporated, the residue is triturated with a little ethyl acetate and filtered off with suction, giving 90 mg (84%) of 2-[3-(2,6-dichlorophenylamino)imidazo-[1,2-a]pyrimidin-2-yl]-3,5-dimethoxybenzohydrazide as hydrochloride; MS-FAB (M+H$^+$)=474.3; $R_f$ (polar method): 1.33 min.

EXAMPLE 4

The preparation of 5-{2-[3-(2,6-dichlorophenylamino)imidazo[1,2-a]-pyrimidin-2-yl]-3,5-dimethoxyphenyl}-3H-1,3,4-oxadiazol-2-one ("A6") is carried out analogously to the following scheme:

115 mg of 2-[3-(2,6-dichlorophenylamino)imidazo[1,2-a]pyrimidin-2-yl]-3,5-dimethoxybenzohydrazide hydrochloride and 26 µl of trichloromethyl chloroformate (diphosgene) are heated under reflux for 2 hours in 5 ml of dioxane. The reaction mixture is evaporated, and water and DCM are added. The aqueous phase is rendered neutral, extracted a number of times with DCM, and the combined organic phases are dried and evaporated. Purification by column chromatography (ethyl acetate/methanol) and washing of the resultant solid by stirring with heptane gives 35 mg (33%) of "A6"; MS-FAB (M+H$^+$)=499.4; $R_f$ (polar method): 1.61 min.

EXAMPLE 5

The preparation of (2,6-dichlorophenyl)-{2-[2,4-dimethoxy-6-(5-methylamino-1,3,4-oxadiazol-2-yl)phenyl]imidazo[1,2-a]pyrimidin-3-yl}amine ("A3") is carried out analogously to the following scheme:

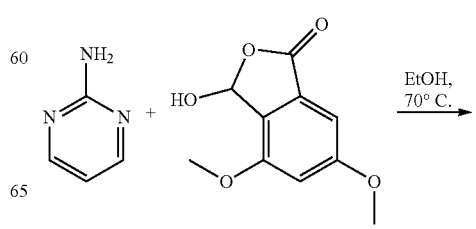

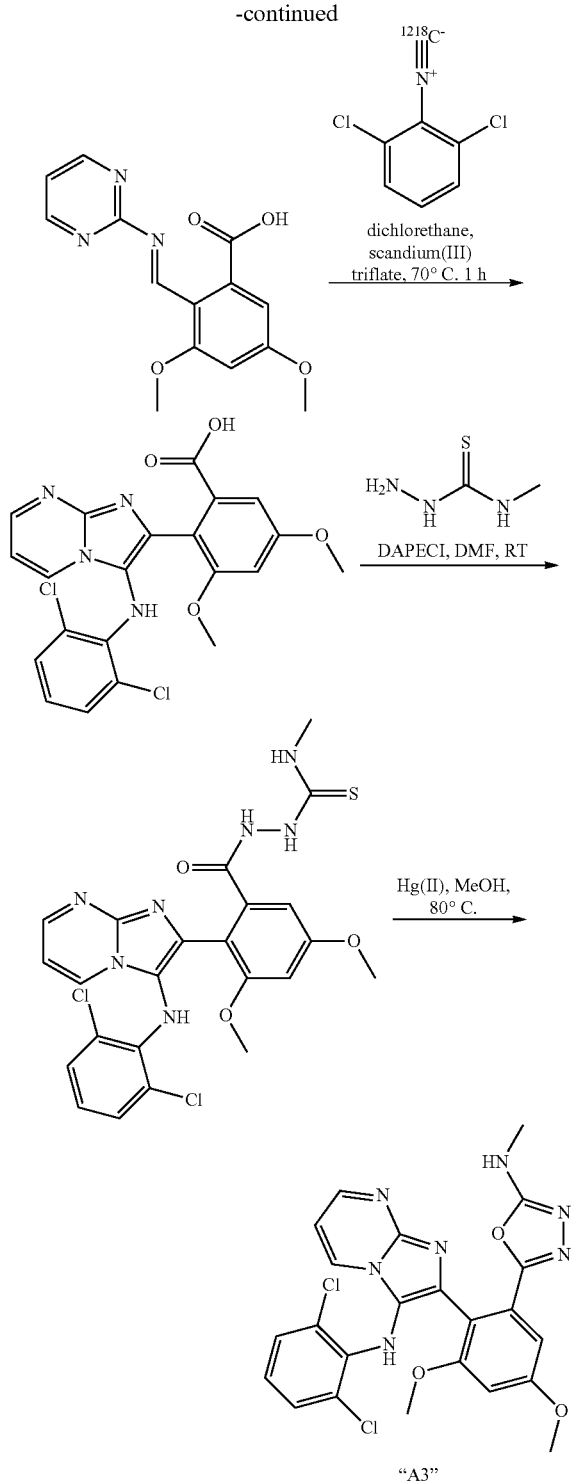

5.1 134 mg of pyrimidin-2-ylamine and 300 mg of 3-hydroxy-4,6-dimethoxy-3H-isobenzofuran-1-one in 6 ml of ethanol are stirred at 70° C. for 24 hours in a screw-lid bottle. The cooled reaction mixture is added to about 20 ml of heptane, during which a precipitate deposits. After separating off and drying, 290 mg of 3,5-dimethoxy-2-[pyrimidin-2-yliminomethyl]benzoic acid (72%) are obtained as white powder; MS-FAB (M+H$^+$)=288.1; R$_f$(HPLC, polar method): 1.85 min.

5.2 72 mg of 1,3-dichloro-2-isocyanobenzene, 100 mg of the imine from step 1 and 86 mg of scandium(III) triflate (anhydrous) are dissolved in 3 ml of dichloroethane and heated at 60° C. for 2 hours. The reaction mixture is evaporated, and the dark residue is purified by silica-gel chromatography (ethyl acetate/methanol), giving, after evaporation of the corresponding fractions, 110 mg of 2-[3-(2,6-dichlorophenylamino)imidazo[1,2-a]pyrimidin-2-yl]-3,5-dimethoxybenzoic acid (69%) as dark solid; MS-FAB (M+H$^+$)=459.2; R$_f$(HPLC, polar method): 1.52 min.

5.3 500 mg of 2-[3-(2,6-dichlorophenylamino)imidazo[1,2-a]pyrimidin-2-yl]-3,5-dimethoxybenzoic acid, 131 mg of 4-methyl-3-thiosemicarbazide and 265 mg of DAPECI (N-3-dimethylaminopropyl-N'-ethylcarbodiimide) are dissolved in 1 ml of DMF and stirred at RT for 16 h. Water is subsequently added, the mixture is extracted three times with DCM, and the organic phase is washed with water. After the organic phase has been dried and the filtrate has been evaporated, 500 mg of the corresponding coupling product remain as solid; MS-FAB (M+H$^+$)=546.4; R$_f$ (HPLC, polar method): 1.70 min. This is employed without further purification in the next step.

5.4 500 mg of the coupling product from step 3 and 381 mg of mercury(II) acetate are stirred at 80° C. for 30 minutes in 5 ml of methanol in a sealed screw-lid bottle. The mixture is filtered through kieselguhr, rinsed with MeOH, and the filtrate is evaporated to dryness. Purification by silicagel chromatography (ethyl acetate/methanol) gives 110 mg of "A3", corresponding to a yield of 24%; MS-FAB (M+H$^+$)= 513.4; R$_f$(HPLC, polar method): 1.54 min.

The following compounds are obtained analogously

| No. | Structure and/or name | MS-FAB (M$^+$) | HPLC (polar) R$_f$ [min] |
|---|---|---|---|
| "A4" | (2,6-Dichloro-4-fluorophenyl)-{2-[2,4-dimethoxy-6-(5-methylamino-1,3,4-oxadiazol-2-yl)phenyl]imidazo[1,2-a]-pyrimidin-3-yl}amine | 531.35 | 1.63 |
| "A5" | (2,6-Dichlorophenyl)-{2-[2-(5-ethylamino-1,3,4-oxadiazol-2-yl)-4,6-dimethoxy-phenyl]imidazo[1,2-a]pyrimidin-3-yl}-amine | 527.38 | 1.65 |
| "A11" | {2-[2,4-Dimethoxy-6-(5-methylamino-1,3,4-oxadiazol-2-yl)phenyl]imidazo-[1,2-a]pyrimidin-3-yl}-(2,6-dimethyl-phenyl)amine | 472.52 | 1.61 |
| "A13" | (2,6-Dichloro-4-fluorophenyl)-{2-[2-(5-methylamino-1,3,4-oxadiazol-2-yl)-phenyl]imidazo[1,2-a]pyrimidin-3-yl}-amine | 471.29 | 1.23 (esilrod) |
| "A14" | (2,6-Dichlorophenyl)-{2-[2-(5-methyl-amino-1,3,4-oxadiazol-2-yl)phenyl]-imidazo[1,2-a]pyrimidin-3-yl}amine | 453.30 | 1.56 |
| "A15" | (2,6-Dichlorophenyl)-{2-[2-(5-ethylamino-1,3,4-oxadiazol-2-yl)phenyl]imidazo-[1,2-a]pyrimidin-3-yl}amine | 467.33 | 1.75 |
| "A16" | {2-[2,4-Dichloro-6-(5-methylamino-1,3,4-oxadiazol-2-yl)phenyl]imidazo[1,2-a]-pyrimidin-3-yl}-(2,6-dimethylphenyl)amine | 481.36 | 1.81 |
| "A19" | {2-[2-Chloro-6-(5-methylamino-1,3,4-oxadiazol-2-yl)phenyl]imidazo[1,2-a]-pyrimidin-3-yl}-(2,6-dimethylphenyl)amine | 446.91 | 1.63 |
| "A21" | (2,6-Dimethylphenyl)-{2-[4-methoxy-2-(5-methylamino-1,3,4-oxadiazol-2-yl)-phenyl]imidazo[1,2-a]pyrimidin-3-yl}-amine | 442.49 | 1.59 |
| "A22" | {2-[2-Chloro-6-(5-methylamino-1,3,4-oxadiazol-2-yl)phenyl]imidazo[1,2-a]-pyrimidin-3-yl}-(2-chloro-6-methylphenyl)-amine | 467.33 | 1.69 |

-continued

| No. | Structure and/or name | MS-FAB (M⁺) | HPLC (polar) R$_f$[min] |
|---|---|---|---|
| "A23" | (2,6-Dichloro-3-methylphenyl)-{2-[2,4-dimethoxy-6-(5-methylamino-1,3,4-oxadiazol-2-yl)phenyl]imidazo[1,2-a]-pyrimidin-3-yl}amine | 527.38 | |
| "A25" | (3,5-Dimethylisoxazol-4-yl)-{2-[2-(5-methylamino-1,3,4-oxadiazol-2-yl)-phenyl]imidazo[1,2-a]pyrimidin-3-yl}-amine | 403.42 | |
| "A26" | (2-Chloro-6-methylphenyl)-{2-[2-fluoro-6-(5-methylamino-1,3,4-oxadiazol-2-yl)-phenyl]imidazo[1,2-a]pyrimidin-3-yl}-amine | 450.88 | 1.61 |
| "A27" | (4-Fluoro-2,6-dimethylphenyl)-{2-[2-fluoro-6-(5-methylamino-1,3,4-oxadiazol-2-yl)phenyl]imidazo[1,2-a]pyrimidin-3-yl}-amine | 448.45 | 1.64 |

Pharmacological Data
Affinity to Receptors

TABLE 1

| Compound No. | SGLT$_1$-IC$_{50}$ | SGLT$_2$-IC$_{50}$ |
|---|---|---|
| "A1" | C | B |
| "A2" | C | C |
| "A3" | A | A |
| "A4" | A | A |
| "A5" | B | A |
| "A6" | C | B |
| "A7" | B | A |
| "A8" | B | B |
| "A9" | C | A |
| "A10" | C | A |
| "A11" | B | A |
| "A12" | C | A |
| "A13" | B | A |
| "A14" | B | A |
| "A15" | B | A |
| "A16" | B | A |
| "A17" | C | B |
| "A18" | C | B |
| "A19" | B | A |
| "A20" | C | A |
| "A21" | C | A |
| "A22" | A | A |
| "A23" | A | A |
| "A24" | A | A |
| "A25" | C | C |
| "A26" | B | A |
| "A27" | B | A |

IC$_{50}$:
10 nM-1 μM = A
1 μM-10 μM = B
>10 μM = C

The following examples relate to pharmaceutical compositions:

EXAMPLE A

Injection Vials

A solution of 100 g of an active compound of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active compound.

EXAMPLE B

Suppositories

A mixture of 20 g of an active compound of the formula I with 100 g of soya lecithin and 1400 g of cocoa butter is melted, poured into moulds and allowed to cool. Each suppository contains 20 mg of active compound.

EXAMPLE C

Solution

A solution is prepared from 1 g of an active compound of the formula I, 9.38 g of NaH$_2$PO$_4$.2H$_2$O, 28.48 g of Na$_2$HPO$_4$.12H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active compound of the formula I are mixed with 99.5 g of Vaseline under aseptic conditions.

EXAMPLE E

Tablets

A mixture of 1 kg of active compound of the formula I, 4 kg of lactose, 1.2 kg of potato starch, 0.2 kg of talc and 0.1 kg of magnesium stearate is pressed to give tablets in a conventional manner in such a way that each tablet contains 10 mg of active compound.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of active compound of the formula I are introduced into hard gelatine capsules in a conventional manner in such a way that each capsule contains 20 mg of the active compound.

EXAMPLE H

Ampoules

A solution of 1 kg of active compound of the formula I in 60 l of bidistilled water is sterile filtered, transferred into ampoules, lyophilised under sterile conditions and sealed under sterile conditions. Each ampoule contains 10 mg of active compound.

The invention claimed is:
1. A compound selected from the following compounds A1 to A27:

| No. | Structure and/or name |
|---|---|
| "A1" | 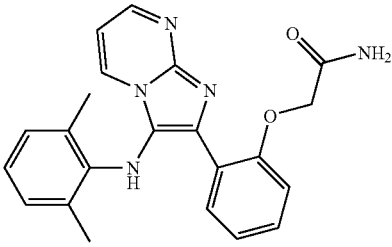<br>2-{2-[3-(2,6-Dimethylphenylamino)imidazo[1,2-a]pyrimidin-2-yl]phenoxy}acetamide |
| "A2" | 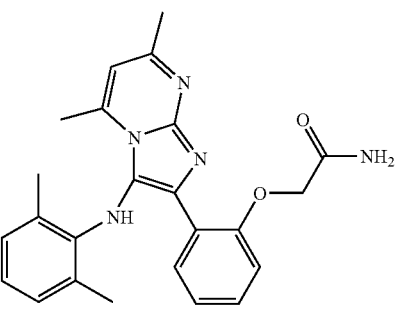<br>2-{2-[3-(2,6-Dimethylphenylamino)-5,7-dimethylimidazo-[1,2-a]pyrimidin-2-yl]phenoxy}acetamide |
| "A3" | (2,6-Dichlorophenyl)-{2-[2,4-dimethyl-6-(5-methylamino-1,3,4-oxadiazol-2-yl)phenyl]imidazo[1,2-a]pyrimidin-3-yl}-amine |
| "A4" | (2,6-Dichloro-4-fluorophenyl)-{2-[2,4-dimethoxy-6-(5-methylamino-1,3,4-oxadiazol-2-yl)phenyl]imidazo[1,2-a]-pyrimidin-3-yl}amine |
| "A5" | (2,6-Dichlorophenyl)-{2-[2-(5-ethylamino-1,3,4-oxadiazol-2-yl)-4,6-dimethoxyphenyl]imidazo[1,2-a]pyrimidin-3-yl}amine |
| "A6" | 5-{2-[3-(2,6-Dichlorophenylamino)imidazo[1,2-a]pyrimidin-2-yl]-3,5-dimethoxyphenyl}-3H-1,3,4-oxadiazol-2-one |
| "A7" | <br>2-{2-[3-(2,6-Dichlorophenylamino)imidazo[1,2-a]pyrimidin-2-yl]-3-ethylphenoxy}acetamide |
| "A8" | 2-{2-[3-(2,6-Dimethylphenylamino)imidazo[1,2-a]pyrimidin-2-yl]-3-ethylphenoxy}acetamide |
| "A9" | 2-{2-[3-(2,6-Dimethylphenylamino)imidazo[1,2-a]pyrimidin-2-yl]-3-ethyl-5-methoxyphenoxy}acetamide |
| "A10" | 2-{2-[3-(2,6-Dimethylphenylamino)imidazo[1,2-a]pyrimidin-2-yl]-5-methoxy-3-methylphenoxy}acetamide |
| "A11" | {2-[2,4-Dimethoxy-6-(5-methylamino-1,3,4-oxadiazol-2-yl)-phenyl]imidazo[1,2-a]pyrimidin-3-yl}-(2,6-dimethylphenyl)-amine |
| "A12" | 2-{2-[3-(2,6-Dichlorophenylamino)imidazo[1,2-a]pyrimidin-2-yl]-3-ethyl-5-methoxyphenoxy}acetamide |
| "A13" | (2,6-Dichloro-4-fluorophenyl)-{2-[2-(5-methylamino-1,3,4-oxadiazol-2-yl)phenyl]imidazo[1,2-a]pyrimidin-3-yl}amine |
| "A14" | (2,6-Dichlorophenyl)-{2-[2-(5-methylamino-1,3,4-oxadiazol-2-yl)phenyl]imidazo[1,2-a]pyrimidin-3-yl}amine |
| "A15" | (2,6-Dichlorophenyl)-{2-[2-(5-ethylamino-1,3,4-oxadiazol-2-yl)phenyl]imidazo[1,2-a]pyrimidin-3-yl}amine |
| "A16" | {2-[2,4-Dichloro-6-(5-methylamino-1,3,4-oxadiazol-2-yl)-phenyl]imidazo[1,2-a]pyrimidin-3-yl}-(2,6-dimethylphenyl)-amine |
| "A17" | 2-[3-(2,6-Dichlorophenylamino)imidazo[1,2-a]pyrimidin-2-yl]-3,5,N-trimethoxybenzamide |
| "A18" | 2-[3-(2,6-Dichlorophenylamino)imidazo[1,2-a]pyrimidin-2-yl]-3,5-dimethoxybenzohydrazide |
| "A19" | {2-[2-Chloro-6-(5-methylamino-1,3,4-oxadiazol-2-yl)phenyl]-imidazo[1,2-a]pyrimidin-3-yl}-(2,6-dimethylphenyl)amine |
| "A20" | 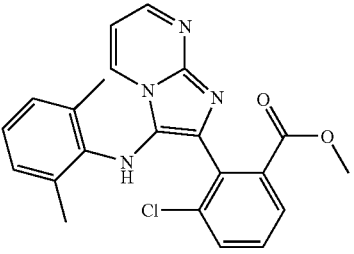<br>Methyl 3-chloro-2-[3-(2,6-dimethylphenylamino)imidazo-[1,2-a]pyrimidin-2-yl]benzoate |
| "A21" | (2,6-Dimethylphenyl)-{2-[4-methoxy-2-(5-methylamino-1,3,4-oxadiazol-2-yl)phenyl]imidazo[1,2-a]pyrimidin-3-yl}-amine |
| "A22" | {2-[2-Chloro-6-(5-methylamino-1,3,4-oxadiazol-2-yl)phenyl]-imidazo[1,2-a]pyrimidin-3-yl}-(2-chloro-6-methylphenyl)-amine |
| "A23" | (2,6-Dichloro-3-methylphenyl)-{2-[2,4-dimethoxy-6-(5-methylamino-1,3,4-oxadiazol-2-yl)phenyl]imidazo[1,2-a]-pyrimidin-3-yl}amine |
| "A24" | 2-[3-(2,6-Dichloro-3-methylphenylamino)imidazo[1,2-a]-pyrimidin-2-yl]-N-ethyl-3,5-dimethoxybenzamide |
| "A25" | (3,5-Dimethylisoxazol-4-yl)-{2-[2-(5-methylamino-1,3,4-oxadiazol-2-yl)phenyl]imidazo[1,2-a]pyrimidin-3-yl}amine |
| "A26" | (2-Chloro-6-methylphenyl)-{2-[2-fluoro-6-(5-methylamino-1,3,4-oxadiazol-2-yl)phenyl]imidazo[1,2-a]pyrimidin-3-yl}-amine |
| "A27" | (4-Fluoro-2,6-dimethylphenyl)-{2-[2-fluoro-6-(5-methyl-amino-1,3,4-oxadiazol-2-yl)phenyl]imidazo[1,2-a]pyrimidin-3-yl}amine | or a pharmaceutically usable salt or stereoisomer thereof, including mixtures thereof in all ratios.

2. A medicament composition comprising at least one compound according to claim 1 or a pharmaceutically usable salt or stereoisomer mixture thereof in all ratios, and optionally excipients and/or adjuvants.

3. A method for treating a patient suffering from type 1 or type 2 diabetes comprising administering to said patient a compound according to claim 1 or a pharmaceutically usable salt or stereoisomer thereof.

4. A method of lowering blood sugar in a patient comprising administering to said patient a compound according to claim 1 or a pharmaceutically usable salt or stereoisomer thereof.

* * * * *